Figure 1:
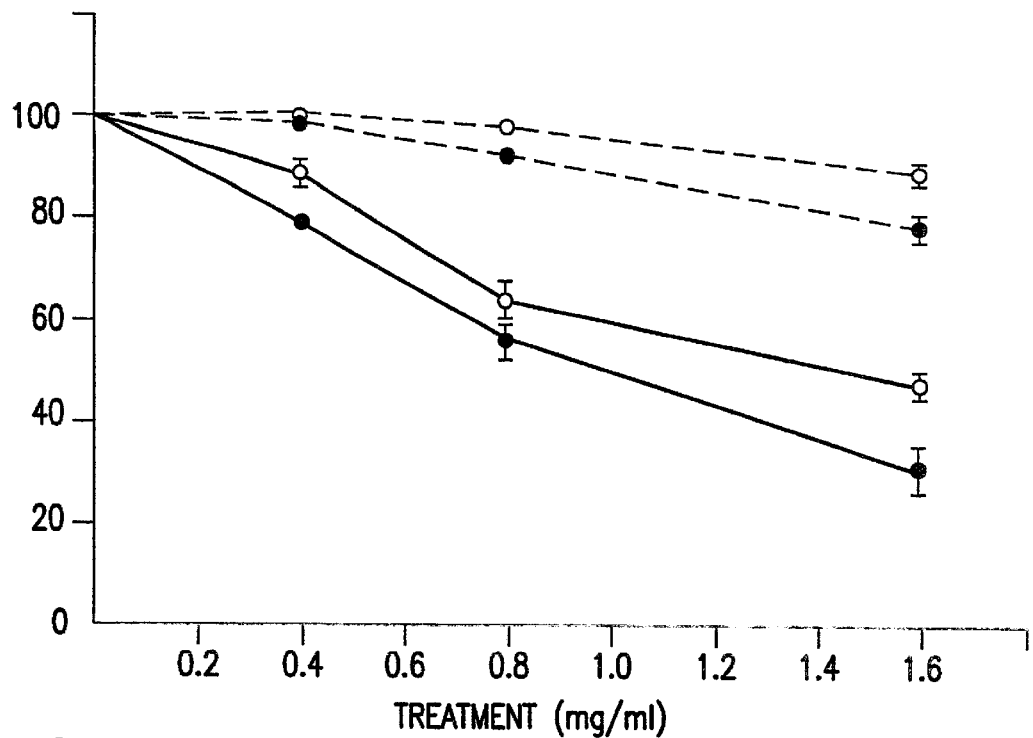

United States Patent [19]
Samid

[11] Patent Number: 6,037,376
[45] Date of Patent: *Mar. 14, 2000

[54] METHODS FOR THERAPY OF CANCER

[75] Inventor: Dvorit Samid, Rockville, Md.

[73] Assignee: The United States of America as represented by the Department of Health and Human Services, Washington, D.C.

[*] Notice: This patent is subject to a terminal disclaimer.

[21] Appl. No.: 07/779,744

[22] Filed: Oct. 21, 1991

[51] Int. Cl.$^7$ .................................................. A61K 31/19
[52] U.S. Cl. ............................................................. 514/568
[58] Field of Search ................................... 514/568, 569, 514/570, 564

[56] References Cited

U.S. PATENT DOCUMENTS

| | | | |
|---|---|---|---|
| 3,973,022 | 8/1976 | Goschke | 424/258 |
| 3,976,673 | 8/1976 | Pifferi | 424/317 |
| 3,998,966 | 12/1976 | Fried et al. | 424/317 |
| 4,028,404 | 6/1977 | Bays et al. | 424/308 |
| 4,282,214 | 8/1981 | Flora et al. | 424/204 |
| 4,457,942 | 7/1984 | Brusilow | 424/317 |
| 4,470,970 | 9/1984 | Burzynski | 424/177 |
| 4,720,506 | 1/1988 | Munkata et al. | |

FOREIGN PATENT DOCUMENTS 1511645    5/1978    United Kingdom .

OTHER PUBLICATIONS

Burzynski, S.R. et al., "Preclinical Studies on Antineoplaston AS2–1 and Antineoplaston AS2–5," *Drugs Exptl. Clin. Res.*, Supplemental 1, XII:11–16 (1986).

Shechter, Y. et al., "Hydroxyphenyl Acetate Derivatives Inhibit Protein Tyrosine Activity and Proliferation in Nb2 Rat Lymphoma Cells and Insulin–Induced Lipogenesis in Rat Adipocytes," *Molecular and Cellular Endrocrinology*, vol. 80, pp. 183–192 (1991).

Samid, D. et al., "Interferon in Combination with Antitumourigenic Phenyl Derivatives: Potentiation of IFN α Activity In–Vitro," *British J. Haematology*, vol. 79, Suppl. 1, pp. 81–83 (Oct. 10, 1991).

Timothy J. Levy, et al., "5–Azacytidine Selectively Increases γ–globin Synthesis in a Patient with β$^+$Thalassemia", New England Journal of Medicine, vol. 307:1469–1475 (Dec. 9, 1982).

Michael B. Sporn, et al., "Chemoprevention of Cancer with Retinoids", Federation Proceedings, vol. 38:2528–2534 (Oct. 1979).

Richard L. Momparler, et al., "Clinical Trial on 5–AZA–2'–Deoxycytidine in Patients with Acute Leukemia", Pharmac. Ther., vol. 30:277–286 (1985).

Gary J. Kelloff, et al., "Chemoprevention Clinical Trials", Mutation Research, vol. 267:291–295 (1992).

I. Bernard Weinstein, "Cancer Prevention: Recent Progress and Future Opportunities", Cancer Research, vol. 51:5080s–5085s (1991).

Olli Simell, et al, "Waste Nitrogen Excretion Via Amino Acid Acylation: Benzoate and Phenylacetate in Lysinuric Protein Intolerance", Pediatr. Res., vol. 20:1117–1121 (1986).

Neish, et al., "Phenylacetic Acid as a Potential Therapeutic Agent for the Treatment of Human Cancer", Experentia, vol. 27:860–861 (1971).

J.A. Stamatoyannopoulos, et al., "Therapeutic Approaches to Hemoglobin Switching in Treatment of Hemoglobinopathies", Annu. Rev. Med., vol. 43:497–521 (1992).

Jones, G.L., *Anti sickling effects of Beta Di Ethylaminoethylidiphenylpropyl acetate SFK–525–A, Phamracologist*, 20(3):204 (1978).

Ross, Philip D. and Subramanian, S., *Inhibition of sickle cell hemoglobin gelation by some aromatic compounds, Biochem. Biophys. Res. Commun.*, 77:1217–1223 (1977).

Erhum, Wilson O., *Acetonyl esters of hydroxybenzoic acids as potential antisickling agents, Niger. J. Pharm.*, 12:285–287 (1981).

Chemical Abstracts 83:53278s (1975).

*Primary Examiner*—Jerome D. Goldberg
*Attorney, Agent, or Firm*—Needle & Rosenberg, P.C.

[57] ABSTRACT

Compositions and methods of treating anemia, cancer, AIDS, or severs β-chain hemoglobinopathies by administering a therapeutically effective amount of phenylacetate or pharmaceutically acceptable derivatives thereof or derivatives thereof alone or in combination or in conjunction with other therapeutic agents. Pharmacologically-acceptable salts alone or in combinations and methods of preventing AIDS and malignant conditions, and inducing cell differentiation are also aspects of this invention.

41 Claims, 4 Drawing Sheets

METHODS FOR THERAPY OF CANCER

I. GOVERNMENT INTEREST

The invention described herein may be manufactured, used and licensed by or for the Government for governmental purposes without the payment to us of any royalties thereon.

II. FIELD OF THE INVENTION

This invention relates to methods of using phenylacetic acid and its pharmaceutically acceptable derivatives as antitumor, and antiviral agents, and treatment of severe beta-chain hemoglobinopathies.

III. BACKGROUND OF THE INVENTION

Some of the most dreadful epidemics, inherited diseases and cancerous infections in the history of mankind are afflicting the world's people at a rapid and discomforting rate. These maladies are being caused in many instances by the increasing cases of cancer, of viral infections, such as human immunodeficiency viruses (HIV) or HTLV and of severe beta-chain hemoglobinopathies. When one pauses to reflect upon the devastating pain, suffering and ultimately death experienced by persons afflicted, these moments of reflection underscore the tremendous importance which must be accorded medical research. In response to the need to alleviate suffering and add comfort to human life, the scientific community throught the world is searching for effective treatments to prevent or ameliorate diseases.

In order to present the enormous scope of this unitary invention in a comprehensive form while preserving the essential need for clarity in presentment, this invention focusing on phenylacetate and its derivatives will be described in the following three (3) subsections, designated herein as A. Phenylacetate In Cancer prevention and maintenance therapy; B. Phenylacetate and its derivatives in the Treatment and Prevention of AIDS; and C. Induction of fetal hemoglobin synthesis in β-chain hemoglobinopathies by phenylacetate and its derivatives.

DESCRIPTION OF RELATED DISCLOSURES

Phenylacetic acid (PAA) is a protein decomposition product found throughout the phylogenetic spectrum, ranging from bacteria to man. Highly conserved in evolution, PAA may play a fundamental role in growth control and differentiation. In plants, PAA serves as a growth hormone (auxin) promoting cell proliferation and enlargement at low doses ($10^{-5}$–$10^{-7}$M), while inhibiting growth at higher concentrations. The effect on animal and human cells is less well characterized. In humans, PAA acid is known to conjugate glutamine with subsequent renal excretion of phenylacetylglutamine (PAG). The latter, leading to waste nitrogen excretion, has been the basis for using PAA or preferably its salt sodium phenylacetate (NaPA) in the treatment of hyperammonemia associated with inborn errors of ureagenesis. Clinical experience indicates that acute or long-term treatment with high NaPa doses is well tolerated, essentially free of adverse effects, and effective in removing excess glutamine. [Brusilow, S. W., Horwich, A. L. Urea cycle enzymes. Metabolic Basis of Inherited Diseases, Vol. 6:629–633 (1989)]. These characteristics should be of value in cancer intervention, treatments to inhibit virus replication and treatment of severe beta-chain hemoglobinopathies.

Glutamine is the major nitrogen source for nucleic acid and protein synthesis, and substrate for energy in rapidly dividing normal and tumor cells. Compared with normal tissues, most tumors, due to decreased synthesis of glutamine along with accelerated utilization and catabolism, operate at limiting levels of glutamine availability, and consequently are sensitive to further glutamine depletion. Considering the imbalance in glutamine metabolism in tumor cells and the ability of PAA to remove glutamine, PAA has been proposed as a potential antitumor agent, however, no data was provided to substantiate this proposal. [Neish, W. J. P. "Phenylacetic Acid as a Potential Therapeutic Agent for the Treatment of Human Cancer", Experentia, Vol. 27, pp. 860–861 (1971)].

Despite efforts to fight cancer, many malignant diseases that are of interest in this application still present a major challenge to clinical oncology. Prostate cancer, for example, is the second most common cause of cancer deaths in men. Current treatment protocols rely primarily on hormonal manipulations, however, in spite of initial high response rates, patients often develop hormone-refractory tumors, leading to rapid disease progression with poor prognosis. Overall, the results of cytotoxic chemotherapy have been disappointing, indicating a long felt need for new approaches to treatment of advanced prostatic cancer. Other diseases resulting from abnormal cell replication for example, metastatic melanomas, brain tumors of glial origin (e.g., astrocytomas), and lung adenocarcinoma, are all highly aggressive malignancies with poor prognosis. The incidence of melanoma and lung adenocarcinoma has been increasing significantly in recent years. Surgical treatment of brain tumors often fails to remove all tumor tissues, resulting in recurrences. Systemic chemotherapy is hindered by blood barriers. Therefore there is an urgent need for new approaches to the treatment of human malignancies such as advanced prostatic cancer, melanoma, brain tumors, and others.

The development of the methods of the present invention was guided by the hypothesis that metabolic traits that distinguish tumors from normal cells could potentially serve as targets for therapeutic intervention. Tumor cells show unique requirements for specific amino acids, of which glutamine would be the desired choice because of its major contribution to energy metabolism and to synthesis of purines, pyrimidines, and proteins. Along this line, promising antineoplastic activities have been demonstrated with glutamine-depleting enzymes such as glutaminase, and various glutamine antimetabolites, unfortunately, the clinical usefulness of these drugs has been limited by unacceptable toxicities. Consequently, the present invention focuses on PAA, a plasma component known to conjugate glutamine in vivo.

In addition to its effect on glutamine phenylacetate can induce tumor cells to undergo differentiation. (See examples 1–5, 8 and 9 herein) Differentiation therapy is a known desirable approach to cancer intervention. The underlying hypothesis is that neoplastic transformation results from defects in cellular differentiation. Inducing tumor cells to differentiate would prevent tumor progression and bring about reversal of malignancy. Several differentiation agents are known, but their clinical applications have been hindered by unacceptable toxicities and/or deleterious side effects.

Accordingly, a major object of the present invention is to provide a method for treating various cancerous conditions with PAA and its pharmaceutically acceptable salts and derivatives.

Another object of the present invention is to provide a method for the prevention of tumor progression and the development of malignant conditions in high risk individuals by administering prophylactically effective amounts of nontoxic agents such as phenylacetate and its pharmaceutically acceptable derivatives.

Another object of the present invention is to provide a method for the amelioration of and prophlactic treatment against viral infections. Still another object of the present invention is to provide a method for the amelioration of and prophylactic treatment against severe anemia associated with beta-chain hemoglobinopathies.

It is yet a further object to provide a method of treating or preventing the onset of malignancies, viral infections associated with AIDS or severe beta-chain hemoglobinopathies with a combination of Phenylacetate (or its pharmaceutically acceptable derivatives) and various other therapeutic or preventive agents alone or in conjunction with conventional therapies.

A further object of the invention is to provide effective pharmaceutical formulations of PAA and its pharmaceutically acceptable derivatives for carrying out the above methods.

IV. BRIEF SUMMARY OF THE INVENTION

The present invention is directed to methods for therapy of cancer. The methods relate to administering a compound or salt of a compound having the formula (I).

The present invention provides a method of (1) suppressing the growth of tumor cells in a host in need of such suppression comprising administering an amount of PAA or a pharmaceutically acceptable derivative thereof effective to suppress the growth of said tumor cells and (2) preventing the onset of or ameliorating the effects of viral infections or severe beta-chain hemoglobinopathies.

For the purpose of the present application, the PAA derivatives include its pharmacological acceptable salts, preferably sodium; analogs containing halogen substitutions, preferably chlorine or fluorine; analogs containing alkyl substitutions, preferably methyl or methoxy; precursors of phenylacetate, preferably phenylbutyrate; and natural analogs such as naphtylacetate.

The compounds of the present invention can be administered intravenously, enterally, parentally, intramuscularly, intranasally, subcutaneously, topically or orally. The dosage amounts are based on the effective inhibitory concentrations observed in vitro and in vivo in antitumorigenicity studies. The varied and efficacious utility of the compounds of the present invention is further illustrated by the finds that they may also be administered concomitantly or in combination with other antitumor agents such as hydroxyurea, 5-azacytidin, 5-aza-2' deoxycytidine, suramin; retinoids; hormones; biological response modifiers, such as interferon and hematopoetic growth factors; and conventional chemo- and radiation therapy or various combinations thereof.

The present invention also provides methods of inducing tumor cell differentiation in a host comprising administering to the host a therapeutically effective amount of PAA or a pharmaceutically acceptable derivative thereof.

The present invention also provides methods of preventing the formation of malignancies by administering to a host a prophylactically effective amount of PAA or a pharmaceutically acceptable derivative thereof.

The present invention also provides methods of treating malignant conditions, such as prostatic cancer, melanoma, adult and pediatric tumors, e.g. brain tumors of glial origin, astrocytoma, Kaposi's sarcoma, lung adenocarcinoma and leukemias, as well as hyperplastic lesions, e.g. benign hyperplastic prostate and papillomas by administering a therapeutically effective amount of PAA or a pharmaceutically acceptable derivative thereof.

V. BRIEF DESCRIPTION OF THE DRAWINGS

FIG. 1 shows the inhibition of HL-60 leukemia and permalignant 10T1/2 cell proliferation by NaPA.

Figure 2:
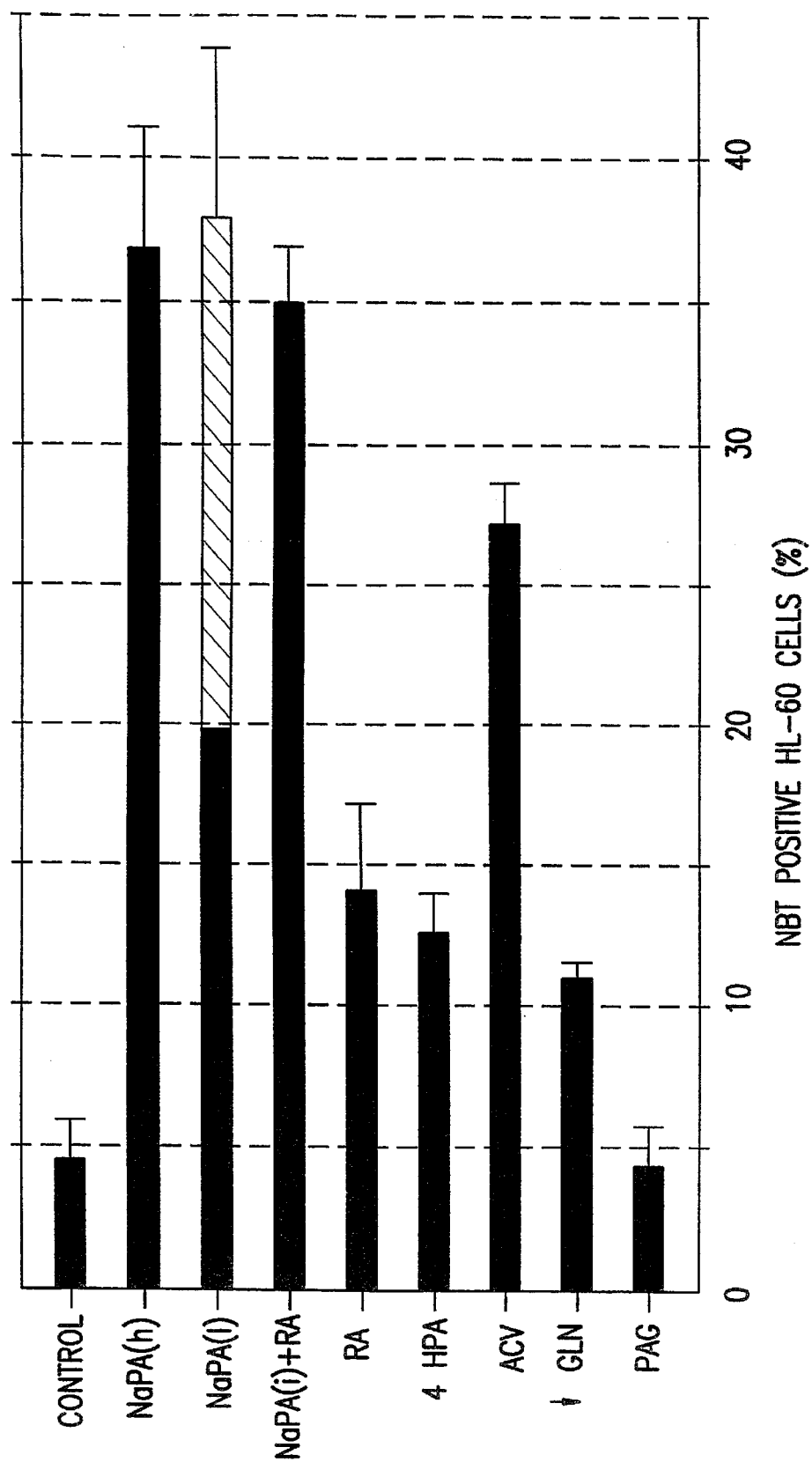

FIG. 2 shows the induction of HL-60 cell differentiation. The number of NBT positive cells was determined after 4 or 7 days of treatment. NaPA (h), 1.6 mg/ml; NaPA (1), 0.8 mg/ml. 4-hydroxy PA and PAG were used at 1.6 mg/ml. Potentiation by RA 10 nM was comparable to that by IFN gamma 300 IU/ml, and the effect of acivicin 3 ug/ml similar to DON 30 ug/ml. Glutamine Starvation (Gln, <0.06 mM) was as described (18). Cell viability was over 95% in all cases, except for DON and acivicin (75% and 63%, respectively).

Figure 3:
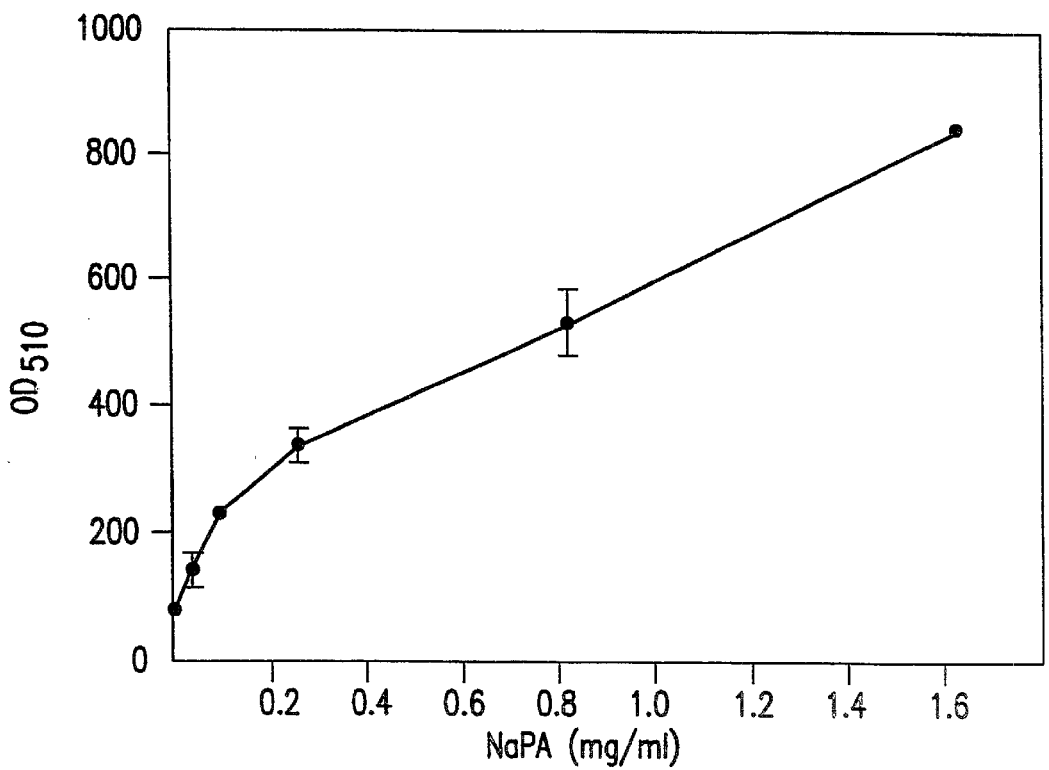

FIG. 3 shows adipocyte conversion in 10T1/2 cultures. Lipids stained with Oil-Red O were extracted with butanol, and the optical density at 510 nm determined. Increased lipid accumulation was evident with NaPA concentrations as low as 0.024 mg/ml.

Figure 4:
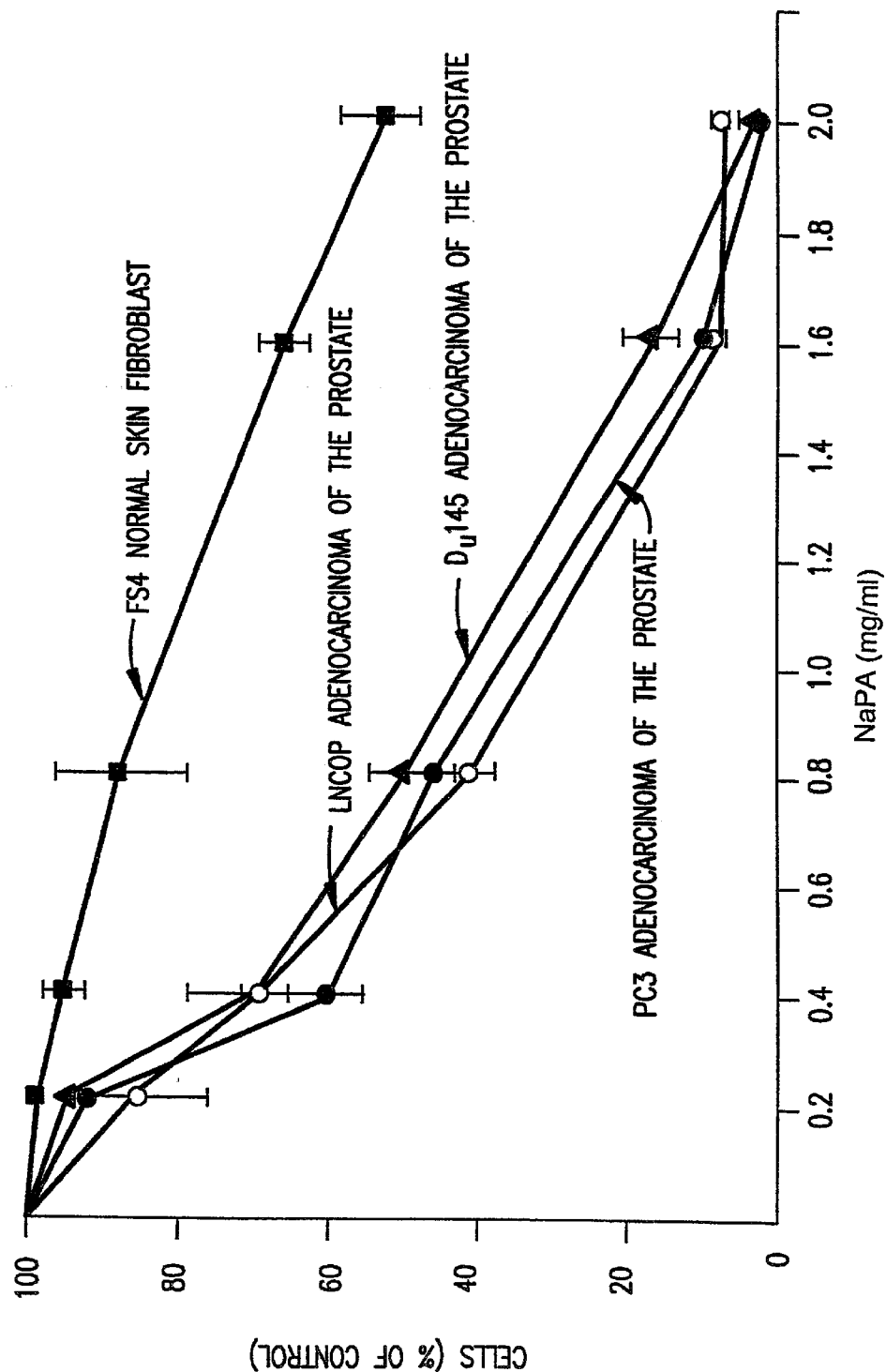

FIG. 4 shows the effect of NaPA on cell proliferation. PC3; DU145; LNCap; and, FS4 cultures were treated with NaPA or PAG for four days.

Figure 5:
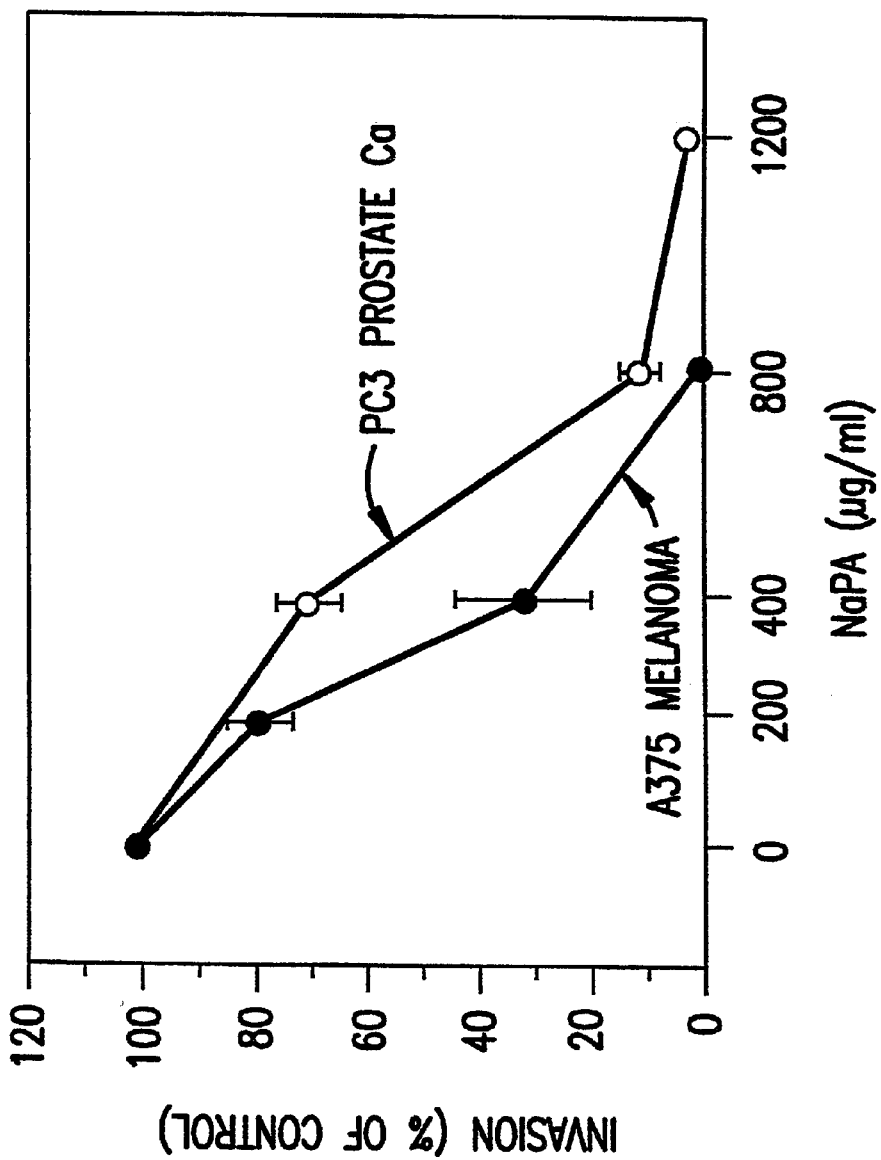

FIG. 5 shows the inhibition of tumor cell invasion by NaPA cells treated in culture for 7 days were harvested and assayed for their invasive properties using a modified Boyder Chamber with a matrigel-coated filter. Results scored 6–24 hours later.

VI. DETAILED DESCRIPTION OF THE INVENTION

According to the present invention, PAA, in particular its sodium salt NaPA has been found to be an excellent inhibitor of the growth of specific tumor cells, affecting the proliferation of the malignant cells while sparing normal tissues. Also, according to the present invention, NaPA has been found to induce tumor cell differentiation, thus offering a most desirable approach to cancer prevention and therapy. Additionally, NaPA has been found to be of potential value for the treatment of AIDS and severe beta-chain hemoglobino-pathies. The exact mechanisms by which the compounds used in the method of this invention exert their effect is uncertain, one mechanism may involve depletion of plasma glutamine. Based on the data reported herein, it is believed that glutamine depletion alone cannot explain the molecular and phenotypic changes observed in vitro following exposure to NaPA. It will be understood, however, that the present invention is not to be limited by any theoretical basis for the observed results. Most significantly, it has now been discovered for the first time:

1. A pharmacetical composition for inhibiting (1) abnormal cell growth and inducing differentiation in nonmalignant or malignant mammalian tumor cells; (2) altering gene expression and inducing differentiation in nonmalignant mammalian cells; or (3) viral replication and spread, comprising a pharmacologically-effective amount of a compound of the formula

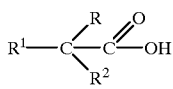

wherein

R and $R^1$ is H, lower alkoxy, or lower alkyl; $R^2$=aryl and substituted aryl; stereoisomers thereof, pharmaceutically-acceptable derivatives or salts thereof; and mixtures thereof.

2. The composition of claim 1, wherein the pharmaceutically-acceptable salts are selected from the group consisting of a alkali and alkaline earth metal.

3. The composition of claim 1, wherein the pharmaceutically-acceptable salt is an alkali metal.

4. The composition of claim 3, wherein the alkalimetal is sodium.

5. The composition of claim 1, wherein R is H and $R^1$ is H, $CH_3$, $CH_3$—O—, $C_2H_5$, or $C_3H_7$.

6. The composition of claim 5 wherein $R^2$ is

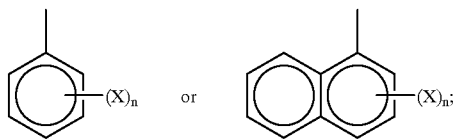

X is halogen or hydroxy; and n is 0 to 4.

7. The composition of claim 6, wherein X is Cl, F, or hydroxy.

8. The composition of claim 7, wherein X is Cl.

9. The composition of claim 8, wherein $R^2$ is

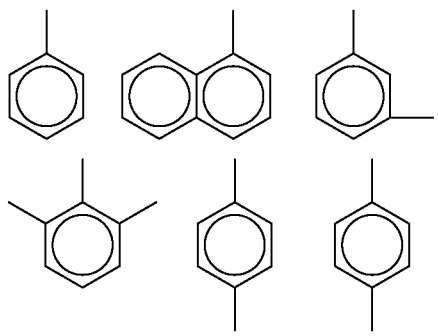

10. The composition of claim 9, wherein R is H or $C_3H_7$ and $R^1$ is H.

11. The composition of claim 10, wherein $R^2$ is

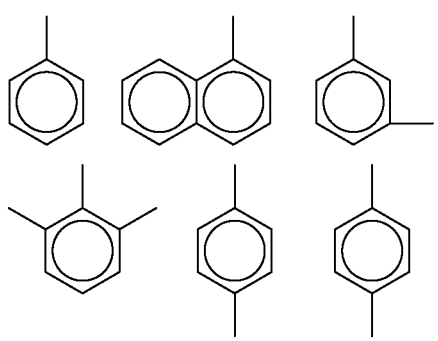

12. The composition of claim 11, wherein $R^2$ is

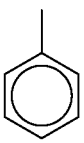

and R is hydrogen.

13. The composition of claim 11 wherein $R^2$ is

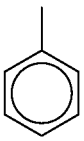

and R is $C_3H_7$.

14. The composition of claim 11, wherein $R^2$ is

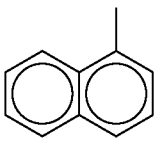

15. The composition of claim 11, wherein $R^2$ is

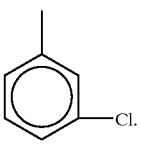

16. The composition of claim 1, comprising about 0.010 to 99.990 weight percent (%) of said compound.

17. A method of inhibiting the growth of rapidly proliferating nonmalignant and malignant mammalian tumor cells, comprising administering to a host in need of said inhibition an amount of the composition of claim 1 effective to attain said inhibition.

18. A method of inhibiting the altering gene expression and inducing differentiating in nonmalignant or malignant mammalian tumor cells in red blood derived from a patient afflicted anemia resulting from abnormal hemoglobin production, comprising administering to host in need of inhibition an inhibitory amount of the composition of claim 1 effective to attain said inhibition.

19. The method of inhibiting viral replication and spread of virus-infected abnormal mammalian cells, comprising administering to a host in need of said inhibition an amount of the composition of claim 1 effective to attain said inhibition.

20. The method of claim 17, wherein said abnormal mammlian cells are red blood derived from a patient afflicted with anemia resulting from abnormal production adult-form hemoglobin.

21. The method of claim 18, wherein the anemic cells are selected from the group comprising sickle cell anemia or beta-thalassemia.

22. The method of claim 19, wherein the virus-infected cell is infected with a retrovirus.

23. The method of claim 22, wherein the retrovirus is a Human Immunodeficiency Virus or HTLV.

24. The method of claim 17, wherein the composition is prophylactically administered prior to the onset of malignancy.

25. The method of claim 24, wherein the composition is prophylactically administered prior to the onset of AID or AIDS-Associated disorders.

26. A method of treating a host afflicted with a condition of cancer, anemia, HIV or HTLV comprising administering to said host a pharmacological amount of the composition of claim 1 effective to ameliorate said conditions.

27. The method in accordance with claim 17 comprising administering to said host an amount of phenylacetic acid or a pharmaceutically acceptable derivative or salt thereof a pharmacologically-effective to suppress the growth of beneign or malignant tumor cells.

28. The method in accordance with claim 18 comprising administering to said host an amount of phenylacetate derivative or salt thereof a pharmalogically-effective to induce the production of the fetal-form hemoglobin.

29. The method according to claim 26, wherein phenylacetic acid or a pharmaceutically acceptable derivative thereof is administered intravenously at a dosage level of from about 50 mg/kg/day to about 100 mg/kg/day.

30. The method according to claim 26, wherein phenylacetic acid or a pharmaceutically acceptable derivative thereof is administered subcutaneously at a dosage level of from about 50 mg/kg/day to about 1000 mg/kg/day.

31. The method according to claim 26, wherein, phenylacetic acid or a pharmaceutically acceptable derivative thereof is administered orally at a dosage level of from about 50 mg/kg/day to about 1000 mg/kg/day.

32. The method according to claim 26, wherein phenylacetic acid or a pharmaceutically acceptable derivative thereof is applied topically at a dosage concentration to about 1 to 10 mg/ml.

33. The method according to claim 26, wherein phenylacetic acid or a pharmaceutically acceptable derivative thereof is administered concomitantly or in combination with an antitumor or antiviral agent.

34. The method according to claim 27, wherein phenylacetic acid or a pharmaceutically acceptable derivative thereof is administered concomitantly or in combination with a biological response modifier.

35. The method according to claim 33, wherein the antitumor agent is selected from the group consisting of hydroxyurea, suramin, retinoids 5-azacytidine and 5-aza-2-deoxcytidine.

36. The method according to claim 33, wherein the the antiviral agent is AZT or DDI.

37. The method according to claim 34, wherein the biological response modifier is selected from the group consisting of interferons, hormones, hormone-antagonists.

38. The method according to claim 26, wherein phenylacetic acid or a pharmaceutically acceptable derivative therof is administered concomitantly or in combination with conventional biotherapy, chemotherapy, hormone manipulation, or radiation therapy.

39. The method according to claim 26, wherein pharmaceutically acceptable derivative is sodium phenylacetate.

40. The method according to claim 26, wherein pharmaceutically acceptable derivative is sodium phenylbutyrate.

41. A method of inducing tumor cell differentiation in a host in need of such treatment comprising administering to said host a therapeutically effective amount of phenylacetic acid or a pharmaceutically acceptable derivative thereof.

42. The method according to claim 41, wherein the anemia is sickle cell or beta-thalassemia.

43. A method of treating malignant conditions comprising administering to a host in need of such treatment a therapeutically effective amount of phenylacetic acid or a pharmaceutically acceptable derivative thereof.

44. A method according to claim 43, wherein the malignant condition to be treated comprises prostatic, melanoma, glial brain tumor, AIDS-Associated Kaposi's Sarcoma and Lymphomas, leukemia, lung adenocarcenoma, brest cancer, osteosarcoma, fibrosarcoma, and squamous cancers.

45. The method of claim 44 provided that $R^{11}$ cannot be phenyl when the condition being treated is brest cancer.

46. The method according to claim 43, wherein the malignant condition to be treated is prostatic cancer.

47. The method according to claim 43, wherein the malignant condition to be treated is melanoma.

48. The method of claim 43 wherein the malignant condition being treated is selected from the group consisting essential of glial brain tumors, AIDS and AIDS associated klaposi's sarcoma and lyphomas.2

VII. EXAMPLES

The herein offered examples, including experiments, provide methods for illustrating, without any implied limitation, the practice of this invention focusing on phenylacetate and its derivatives directed to A. Cancer therapy and prevention; B. Treatment and prevention of AIDS; and C. Induction of fetal hemoglobin synthesis in β-chain hemoglobinopathies.

SECTION A.

PHENYLACETATE IN CANCER PREVENTION AND MAINTENANCE THERAPY

Recent advances in molecular techniques allow the detection of genetic disorders associated with predisposition to cancer. Consequently, it is now possible to identify high-risk individuals as well as patients in remission with residual disease. Despite such remarkable capabilities, there is no acceptable preventive treatment. Chemopreventive drugs are needed also for adjuvant therapy, to minimize the carcinogenic effects of the prevailing anticancer agents and maintain tumor responses.

To qualify for use in chemoprevention, a drug should have antitumor activities, be nontoxic and well tolerated by humans, easy to administer (orally), and inexpensive. We suggest that NaPA may possess all of the above characteristics.

Experimental Data

1. Prevention of Neoplastic transformation—Oncogene transfer studies.

NIH 3T3 cells carrying activated EJras oncogene (originally isolated from human bladder carcinoma) were used as a model to study the potential benefit of NaPA treatment to high risk individuals, in which predisposition is associated with oncogene activation. Cell treatment with NaPA was initiated 24–48 hr after oncogene transfer. Results, scored 14–21 days later, showed dose-dependent reduction in the formation of ras-transformed foci in cultures treated with NaPA. Molecular analyses indicated that the drug did not interfere with oncogene uptake and transcription, but rather prevented the process of neoplastic transformation. The effect was reversible upon cessation of treatment. In treated humans, however, the fate of the premalignant cells may be substantially different due to involvement of humoral and cellular immunity (see below).

2. Prevention of tumor progression by genotoxic chemotherapy

Current approaches to combat cancer rely primarily on the use of chemicals and radiation, which are themselves carcinogenic and may promote recurrences and the development of metastatic disease. One example is the chemotherapeutic drug 5-aza-2' deoxycytidine (5Azadc). While this drug shows promise in treatment of some leukemias and severe inborn anemias, the clinical applications have been hindered by concerns regarding toxicity and carcinogenic effects. Our data indicate that NaPA can prevent tumor progression induced by 5azadC.

The experimental model involved non malignant 4C8a10 cells (revertants of Ha-ras-transformed NIH3T3 fibroblasts). Transient treatment of the premalignant cells with 5AzadC resulted in malignant conversion evident within 2 days, as determined by cell morphology, loss of contact inhibition and anchorage dependent growth in culture, acquired invasive properties and tumorigenicity in recipient athymic mice. Remarkably, NaPA prevented the development of the malignant phenotype in the 5AzadC treated cultures.

TABLE 1

| Treatment | Tumor Formation[a] | | Growth on matrigel[b] |
| --- | --- | --- | --- |
| | Incidence | Size (mm) | |
| None | 3/8 | 1 (0.5–2) | – |
| 5Azadc (0.1 uM) | 8/8 | 11.5 (4–19) | + |
| NaPA (1.5 mg/ml) | 0/8 | | – |
| 5Azadc + NaPA (0.1 uM) (1.5 mg/ml) | 0/8 | 0 | – |

[a]Cells pretreated in culture were injected s.c. ($5 \times 10^5$ cells per site) into 3 month old female athymic nude mice (Division of Cancer Treatment, NCI animal Program, Frederick Cancer Research Facility). Results indicate the incidence (tumor bearing/injected animals), as well as tumor size as mean (range), determined after 3 weeks.
[b]Cells were plated on top of matrigel (reconstituted basement membrane) and observed for malignant growth pattern, i.e., active replication, development of characteristic processes, and invasion.

Anticipated Activity in Humans.

In terms of cancer prevention, the beneficial effect of NaPA humans may be even more dramatic than that observed with the experimental models. In humans, NaPA is known to deplete circulating glutamine, an aminoacid critical for the development and progression of cancer. The enzymatic reaction leading to glutamine depletion takes place in the liver and kidney; it is not clear whether or not glutamine depletion occurs in the cultured tumor cells. Moreover, molecular analysis revealed that NaPA can induce the expression of histocompatibility class I antigens, which are localized on the surface of tumor cells and affect the immune responses of the host. While the therapeutic benefit of NaPA observed in cultures is in some cases reversible upon cessation of treatment, in patients the tumor cells might eventually be eliminated by the immune system. Even if chemoprevention will require continuous treatment with NaPA, this would be acceptable considering the lack of toxicity.

Pharmaceutical compositions containing phenylacelate have been shown to cause reversal of malignancy and to induce differenciation of tumor cells. To demonstrate the capacity of drugs to induce differentiation of tumor cells, three in vitro differentiation model systems were used. (See sections A and D herein) The first system used a human promyelocytic leukemia cell line HL-60. This cell line represents uncommitted precursor cells that can be induced to terminally differentiate along the myeloid or monocytic lineage. In the second system, immortalized embryonic mesenchymal C3H 10T1/2 cells were used which have the capabilities of differentiating into myocytes, adipocytes, or chondrocytes. In the third system, human erythroleukemia cells (K562) were used which can be induced to produce hemoglobin.

EXAMPLE 1

Referring now to the data obtained using the first system, the results of which are illustrated in FIG. 1, logarithmically growing HL-60 [—○—] and 10T1/2 [—○—] cells were treated for four days with NaPA [++] or phenylacetylglutamate (PAG) [- - -]. The adherent cells were detached with trypsin/EDTA and the cell number determined using a hemocytometer. Data points indicate the mean±S.D. of duplicates from two independent experiments. The cell lines were obtained from the American Type Culture Collection and maintained in RPMI 1640 (HL-60) or Dulbecco's Modified Eagle's Medium (10T1/2) supplemented with 10% heat inactivated fetal calf serum (Gibco Laboratories), 2 mM L-Glutamine, and antibiotics. PAA (Sigma, St. Louis Mo.) and PAG were each dissolved in distilled water, brought to pH 7.0 by the addition of NaOH, and stored in −20° C. until used. As demonstrated in FIG. 1, NaPA treatment of the HL-60 and 10T1/2 cultures was associated with dose dependent inhibition of cell proliferation.

EXAMPLE 2

To further evaluate the effectiveness of NaPA as an inducer of tumor cell differentiation, the ability of NaPA to induce granulocyte differentiation in HL-60 was investigated. The ability of cells to reduce nitroblue tetrazolium (NBT) is indicative of oxidase activity which is characteristic of the more mature forms of human bone marrow granulocytes. NBT reduction thus serves as an indicator of granulocyte differentiation. In FIG. 2, the number of NBT positive cells was determined after 4 days [solid bars] or 7 days [hatched bar] of treatment. NaPA (h), 1.6 mg/ml; NaPA (1), 0.8 mg/ml. 4-hydroxyphenylacetate (4HPA) and PAG were used at 1.6 mg/ml. Potentiation by retinoic acid (RA) 10 nM was comparable to that by interferon gamma 300 IU/ml. The direction of differentiation towards granulocytes in cultures treated with NaPA, whether used alone or in combination with RA, was confirmed by microscopic evaluation of cells stained with Wright Stain and the lack of nonspecific esterase activity. The effect of acivicin (ACV) 1 ug/ml was similar to 6-diazo-5-oxo-L-norleucine (DON) 25 ug/ml. Glutamine starvation (Gln, <0.06 mM) was as described. Cell viability determined by trypan blue exclusion was over 95% in all cases, except for DON and ACV which were 75% and 63%, respectively. DON, ACV and HPA are glutamine antagonists. As illustrated in FIG. 2, it is clear that NaPA is capable of inducing granulocyte differentiation in HL-60. As further illustrated in FIG. 2, differentiation of HL-60, assessed morphologically and functionally, was sequential and could be further enhanced by the addition of low doses of retinoic acid (RA, 10 nM) or interferon gamma (300 IU/ml). After seven days of NaPA treatment, or four days, when combined with RA, the HL-60 cultures were composed of early stage myelocytes and metamyelocytes (30–50%), as well as banded and segmented neutrophils (30–40%) capable of NBT.

Pharmacokinetics studies in children with urea cycle disorders indicate that infusion of NaPA 300–500 mg/kg/day, a well tolerated treatment, results in plasma levels of approximately 800 ug/ml. Brusilow, S. W. et al. Treatment of episodic hyperammonemia in children with inborn errors of urea synthesis. The New England Journal of Medicine. 310:1630–1634 (1984). This same concentration was shown to effectively induce tumor cell differentiation in the present experimental system.

EXAMPLE 3

That NaPA is capable of inducing adipocyte conversion in 10T1/2 cultures is illustrated in FIG. 3. The results in FIG.

3 show that differentiation was dose and time-dependent, and apparently irreversible upon cessation of treatment. NaPA at 800 ug/ml was quite efficient and totally free of cytotoxic effect. In the 10T1/2 model, adipocyte conversion involved over 80% of the cell population. It was noted that higher drug concentrations further increased the efficiency of differentiation as well as the size of lipid droplets in each cell.

It is known that glutamine conjugation by NaPA is limited to humans and higher primates and that in rodents NaPA binds glycine. [James, M. O. et al. The conjugation of phenylacetic acid in man, sub-human primates and some nonprimate species. Proc. R. Soc. Lond. B. 182:25–35 (1972). Consequently, the effect of NaPA on the mouse 10T1/2 cell line could not be explained by an effect on glutamine. In agreement, neither glutamine starvation nor by treatment with glutamine antagonists such as DON and ACV resulted in adipocyte conversion.

EXAMPLE 4

TABLE 2

Phenylacetate and Derivatives: Induction of cellular differentiation in premalignant 10T1/2 cells

| Compounds<br>DC50*<br>(sodium salts)<br>(mM) | | Differentiation<br>at 1 mM<br>(%) |
| --- | --- | --- |
| Phenylacetate | 65 | 0.7 |
| 1-naphthylacetate | >95 | <0.1 |
| 3-chlorophenylacetate | 80 | 0.5 |
| 4-chlorophenylacetate | 50 | 1.0 |
| 2,6-dichlorophenylacetate | 75 | 0.5 |
| 4-fluorophenylaceatae | 65 | 0.7 |

*DC50, concentration of compound causing 50% differentiation

Potential clinical use of phenylacetate and derivatives

As shown in the table, phenylacetate and its derivatives efficiently induced lipid accumulation and adipocyte (fat cell) differentiation in premalignant cells. This and other results indicate that the tested compounds might be of value in:
1. Cancer prevention. Non replicating, differentiated tumor cells are not likely to progress to malignancy.
2. Differentiation therapy of malignant and phathological nonmalignant conditions.
3. Treatment of lipid disorders, in which patients would benifit from increased lipid accumulation.
4. Wound healing. This is indicated by the ability of phenylacetate to induce collagen synthesis in fibroblasts (shown in FIG. 13).

It is known that studies in plants reveal that NaPA can interact with intracellular regulatory proteins and modulate cellular RNA levels. In an attempt to explore the possible mechanism of action, Northern blot analysis of HL-60 and 10T1/2 cells was performed according to conventional methods. As shown in FIG. 4a, cytoplasmic RNA was extracted, separated and analyzed (20 ≦g/lane) from confluent cultures treated for 72 hrs with NaPA or PAG (mg/ml); C is the untreated control. The aP2 cDNA probe was labeled with [32P]dCTP (NEN) using a commercially available random primed DNA labeling kit. Ethidium bromide-stained 28S rRNA indicates the relative amounts of total RNA in each lane.

The results of the Northern blot analysis of HL-60 and 10T1/2 cells, showed marked changes in gene expression shortly after NaPA treatment. Expression of the adipocyte-specific aP2 gene was induced within 24 hrs in treated 10T1/2 confluent cultures reaching maximal mRNA levels by 72 hrs.

EXAMPLE 5

In HL-60, cell transformation has been linked to myc amplification and overexpression, and differentiation would typically require down regulation of myc expression. [Collins, S. J. The HL-60 promyelocytic leukemia cell line: Proliferation, differentiation, and cellular oncogene expression. Blood. 70:1233–1244 (1987)]. To demonstrate the kinetics of myc inhibition and HLA-A induction, Northern blot analysis of cytoplasmic RNA (20 ug/lane) was carried out on cells treated with NaPA and PAG for specified durations of time and untreated controls (−). Two concentrations of NaPA, 1.6 mg/ml (++) and 0.8 mg/ml (+), and PAG at 1.6 mg/ml was investigated. The 32P-labeled probes used were myc 3rd exon (Oncor) and HLA-A3 Hind III/EcoRI fragment. NaPA caused a rapid decline in the amounts of myc mRNA. This occurred within 4 hours of treatment, preceding the phenotypic changes detectable by 48 hrs, approximately two cell cycles, after treatment. Similar kinetics of myc inhibition have been reported for other differentiation agents such as dimethyl sulfoxide, sodium butyrate, bromodeoxyuridine, retinoids, and 1,25-dihydroxyvitamin D3. The results suggest that down regulation of oncogene expression by NaPA may be responsible in part for the growth arrest and induction of terminal differentiation. In addition, NaPA treatment of the leukemic cells was associated with time- and dose-dependent accumulation of HLA-A mRNA coding for class I major histocompatibility antigens. It is believed that this may enhance the immunogenicity of tumors in vivo.

EXAMPLE 6

Further support for the use of NaPA as a non-toxic inducer of tumor cell differentiation was found in the ability of NaPA to promote hemoglobin biosynthesis in erythroleukemia cells. It is known that K562 leukemic cells have a nonfunctional betta globin gene and, therefore, do not normally make much hemoglobin. When K562 human erythroleukemia cells were grown in the presence of NaPA at 0.8 and 1.6 mg/ml concentrations, hemoglobin accumulation, a marker of differentiation, was found to increase 4–9 fold over the control cells grown in the absence of NaPA. Hemoglobin accumulation was determined by Benzidine staining of cells for hemoglobin and direct quantitation of the protein.

It has been shown that high concentrations of NaPA inhibit DNA methylation in plants. [Vanjusin, B. J. et al. Biochemia 1,46:47–53 (1981)]. Alterations in DNA methylation can promote oncogenesis in the evolution of cells with metastatic capabilities. [Rimoldi, D. et al. Cancer Research. 51:1–7 (1991)]. These observations raised some concerns regarding potential long-term adverse effects with the use of NaPA. To determine the potential tumorigenicity of NaPA, a comparative analysis was performed using NaPA and a known hypomethylating agent 5-aza-2'-deoxycytidine (5AzadC).

Premalignant cells (3–4×105) were plated in 75 cm2 dishes and 5AzadC 0.1 uM was added to the growth medium at 20 and 48 hrs after plating. The cells were then subcultured in the absence of the nucleoside analog for an additional seven weeks. Cells treated with NaPA at 1.6 mg/ml were subcultured in the continuous presence of the drug. For the tumorigenicity assay, 4–5 week-old female athymic nude mice were inoculated s.c. with 1×106 cells and observed for tumor growth at the site of injection.

The results set forth in Table 1 show that NaPA, unlike the cytosine analog, did not cause tumor progression.

TABLE 3

Tumorigenicity of C3H 10T1/2 Cells in Athymic Mice

| Treatment Time (weeks) | Tumors Incidence (positive/ injected mice) | Diameter (mm ± − S.D.) |
| --- | --- | --- |
| None | 0/8 | 0 |
| 5 AzadC | 8/8 | 5.5 ± 2.5 |
| NaPA | 0/8 | 0 |

The transient treatment of actively growing 10T1/2 cells with 5AzadC resulted in the development of foci of neoplastically transformed cells with a frequency of about 7×10−4. These foci eventually became capable of tumor formation in athymic mice. By contrast, actively replicating 10T1/2 cultures treated for seven weeks with NaPA, 800–1600 ug/ml, differentiated solely into adipocytes, forming neither neoplastic foci in vitro nor tumors in recipient mice.

Furthermore, experiments have demonstrated that NaPA can prevent spontaneous or 5AzadC-induced neoplastic transformation, thus suggesting a potential role in cancer prevention. It is known that the treatment of premalignant 4C8 and 10T1/2 cells with carcinogens such as 5AzadC produces malignant conversion of the respective cells. When 4C8 [Remold: et al., Cancer Research, 51:1–7 (1990)] and 10T1/2 cells were exposed to 5AzadC, malignant conversion was evident in two days and two weeks, respectively. NaPA (0.8–1.6 mg/ml) prevented the appearance of the malignant phenotype, as determined by cell morphology, contact inhibition and anchorage dependent growth in culture. Additionally, see section B, herein.

EXAMPLE 7

The K562 erythroleukemia line serves as a model for inherited anemias that are associated with a genetic defect in the beta globin gene leading to severe B-chain hemoglobinopathies.

The results reported in Table 3 also show that there is a synergistic affect when leukemia cells are exposed NaPA in combinaiton with interferon alpha, a known biological response modifier or with the chemotherapeutic drug hydroxyurea (HU).

TABLE 4

Induction of Hemoglobin Synthesis in Erythroleukemia K562 cells

| TREATMENT | BENZIDINE POSITIVE CELLS* (%) | CELL VIABILITY (%) |
| --- | --- | --- |
| Control | 1.8 | >95 |
| NaPA 0.8 mg/ | 6.0 | |
| 1.6 mg/ml | 17.1 | |
| Interferon 500 IU/ml | 13.5 | |
| HU 100 uM | 17.2 | |
| NaPA (0.8 mg/ml) + HU or IFN | 40–42 | |

*Results at seven days of treatment.

Analysis of gene transcripts showed accumulation of mRNA coding for gamma globin, the fetal form of globin. This was confirmed at the protein level.

Using the erythroleukemia K562 cell line described above it was found that 4 hydroxyphenylacetate was as effective as NaPA in inducing fetal hemoglobin accumulation, but was less inhibitory to cell proliferation. In contrast, some other analogs such as 2,4- or 3,5-dihydroxyphenylacetate were found to be highly toxic (Please see section III, herein for further discussion).

EXAMPLE 8

The effectiveness of NaPA as an antitumor agent was further evaluated in a variety of experimental models. Studies of depth were performed with two androgen- independent human prostate adenocarcinoma cell lines, PC3 and DU145, established from bone and brain metastases, respectively. NaPA treatment of the prostatic cells resulted in concentration-dependent growth arrest, accompanied by cellular swelling and accumulation of lipid. The results of this study are shown in FIG. 4. As illustrated therein, an IC50 for NaPA occurred at 600–800 ug/ml. Significantly higher doses were needed to affect the growth of actively replicating normal human FS4 skin fibroblasts, indicating a selective cytostatic effect of the drug.

EXAMPLE 9

It is known that PC3 cells are invasive in vitro and metastatic in recipient athymic mice. [Albini, A. et al. A rapid in vitro assay for quantitating the invasive potential of tumor cells. Cancer Res. 47:3239–3245 (1987)]. The invasiveness of PC3 cells which is indicative of their malignant phenotype can be assessed by their ability to degrade and cross tissue barriers such as matrigel, a reconstituted basement membrane. Untreated PC3 cells and PC3 cells treated with NaPA for 4 days in culture were quantitatively analyzed in a modified Boyden chamber containing a matrigel-coated filter with FS4 conditioned medium as a chemoattractant. After 4 days of treatment with 800 ug/ml of NaPA in T.C. plastic dishes, 5×10$^4$ cells were replated onto 16 mm Costar dishes coated with 250≦1 of matrigel. Pictures of controls taken after 1 and 8 days, show the characteristic growth pattern of untreated cells, i.e., formation of net-like structures composed of actively replicating cells which eventually degraded the matrigel and formed monolayers on the plastic surface beneath. In contrast to the controls, the NaPA treated cells formed isolated small colonies which resembled normal human FS4 cells as shown in C and D taken 8 days after plating. The NaPA treated cells failed to degrade the matrigel barrier. The formation of small noninvasive colonies on top of the matrigel is indicative of loss of malignant properties following treatment. Results of the in vitro invasion assays correlate highly with the biological behavior of cells in vivo.

EXAMPLE 10

Indeed, PC3 cells treated with NaPA for one week in culture, in contrast to untreated cells or those treated with PAG, failed to form tumors when transplanted s.c. into athymic mice. These results are shown in Table 5.

TABLE 5

Tumorigenicity of Prostatic PC3 Cells in Nude Mice.

| TREATMENT (mg/ml) | TUMORS Incidence | Diameter (mm ± S.D.) | Weight (mg) |
|---|---|---|---|
| None | 7/7 | 9 ± 3 | 285 ± 60 |
| NaPA 0.8 | 1/7 | 2 | 50 |
| PAG 0.8 | 3/4 | 8 ± 2 | 245 ± 35 |

PC3 cells were pretreated for 1 week in culture and then injected ($2 \times 10^5$ cells/animal) s.c. into 4–5 week-old female athymic nude mice. The results in Table 5 indicate the incidence of tumor bearing animals/injected animals as well as tumor size measured as mean diameter ±S.D. 8 weeks later. The data in Table 4 are a summary of two independent experiments.

EXAMPLE 11

To further substantiate the phenotypic changes observed in the NaPA treated prostatic PC3 cells, Northern blot analysis revealed that NaPA inhibited the expression of collagenase type IV, one of the major metalloproteases implicated in degradation of basement membrane components, tumor cell invasion, and metastasis. Furthermore, it was found that NaPA treated prostatic PC3 cells showed an increase in the level of HLA-A mRNA which codes for major histocompatibility class I antigen known to affect tumor immunogenicity in vivo.

NaPA in Combination with Suramin

TABLE 6

Malignant Melanoma A375

| Treatment (ug/ml) | | Growth (% of control) | Viability (%) |
|---|---|---|---|
| None | | 100 | >95 |
| NaPA 400 | | 63.3 | >95 |
| Suramin | 38 | 78.3 | >95 |
| | 75 | 56.8 | >95 |
| | 150 | 38.6 | 92 |
| | 300 | 26.6 | 82 |
| NaPA (400) | + Suramin (38) | 45.5 | >95 |
| | + Suramin (75) | 30.1 | 94 |
| | + Suramin (150) | 21.8 | 92 |

TABLE 7

Prostate Adenocarcinoma PC3

| Treatment (ug/ml) | | Growth (% of control) | Viability (%) |
|---|---|---|---|
| None | | 100 | >95 |
| NaPA 800 | | 59.6 | >95 |
| Suramin | 75 | 58.5 | nd |
| | 150 | 46.5 | nd |
| | 300 | 31.0 | nd |
| NaPA (800) | + Suramin (75) | 24.2 | 90 |
| | + Suramin (150) | 10.9 | 64 |

NaPA was found to significantly potentiate the therapeutic effect of suramine, the only experimental drug known to be active against prostate cancer.

It is known that a disease state characterized by the presence of benign hyperplastic lesions of the prostate exists as a separate disease entity and has been identified in many patients that progress to a diagnosis of prostatic cancer. Based on the above, it is anticipated that NaPA, in addition to being effective in the treatment of prostatic cancer, would be effective in treating patients having benign hyperplastic prostatic lesions.

Further experiments demonstrated that NaPA appears to have broad antitumor activity affecting a wide spectrum of malignancies. The experimental data indicate presented in Table 5 that NaPA 0.4–0.8 mg/ml caused about 50% inhibition of growth in treated adenocarcinoma of the prostate cell lines PC3 and DU145, melanoma A375 and SK MEL 28, lung adenocarcinoma H596 and H661, and astrocytoma U87, U373, and 343. Somewhat higher concentrations (1.0–1.5 mg/ml) were needed to cause a similar inhibition of squamous cell carcinoma A431, breast tumor MCS-7, osteosarcoma KRIB, and fibrosarcoma V7T. Typically, NaPA treatment was associated with growth arrest, induction of differentiation markers, reduced invasiveness in vitro, and loss of tumorigenicity in nude mice.

TABLE 8

RESPONSES OF DIFFERENT TUMOR CELL LINE TO NaPA TREATMENT

| # | Tumor Cell Line | | % Inhibition by NaPA 0.8 mg/ml a |
|---|---|---|---|
| 1 | Melanoma | A375 | ≧70 |
| | | SK MEL 28 | >50 |
| 2 | Prostatic Ca b | PC3 | ≧50 |
| | | Du145 | ≧50 |
| | | LaNCoP | >50 |
| 3 | Astrocytoma | U87 | ≧50 |
| | | U343 | ≧50 |
| | | U373 | ≧50 |
| 4 | Kaposi's Sarcoma | KS | ≦40 |
| 5 | Leukemia | HL-60 | ≦40 |
| 6 | Leukemia | K562 | ≦30 |
| 7 | Breast Ca. | MCF-7 | ≦30 |
| 8 | Osteosarcoma | KRIB | ≦30 |
| | | HOS | <20 |
| 9 | Fibrosarcoma | V7T | ≦30 |
| | | RS485 | ≦30 |
| 10 | Squamous Ca. of Head & Neck | A431 | <30 | a Pharmacologically attainable concentration
b Carcinoma

Of major interest in Table 4 are the following:

1–3 Tumor cells show significant response i.e., ≧50 inhibition of proliferation within one week of treatment.

4 KS, an HIV-associated disorder, may be more dramatically affected by NaPA in humans, due to inhibition of HIV expression and of essential growth factors released by infected lymphocytes.

5,6 The treated HL-60 promyelocytic leukemic cells undergo terminal differentiation, a desirable outcome of chemotherapy. In the K562 erythroleukemia, NaPA induced reversible erythroid diferentation with no significant growth arrest (<30); thus the K562 data is of interest with respect to treatment of certain anemias, not cancer.

Less attractive:

7–10 For effective responses, the tumors may require much higher drug concentrations if used alone.

Although some of the malignant cell lines seem more sensitive than others, all were significantly more affected by NaPA when compared to normal or benign cells. For example, NaPA inhibited the growth of malignant osteosarcoma (KRIB) cells more so than benign osteosarcoma-derived HOS cells. A differential effect was seen also in ras-transformed fibrosarcoma V7T, when compared to the parental non-tumorigenic N1H3T3 cells. As to normal human cells, as much as 2–4 mg/ml of NaPA were needed to cause a significant inhibition of growth to primary human skin FS4 fibroblasts. It should be noted that the treatment was not toxic to either the malignant or the normal cells.

The concentration range found to selectively suppress malignant growth can be readily obtained in the clinical setting without causing significant side effects. Intravenous infusion of humans with NaPA at 250–500 mg/kg/day which results in plasma levels of 600–800 ug/ml has been found to be a well tolerated treatment. Cytotoxicity in tissue culture was observed when the NaPA concentration was >3 mg/ml.

SECTION B
PHENYLACETATE AND ITS DERIVATIVES IN THE TREATMENT AND PREVENTION OF AIDS

The etiology of human acquired immunodeficiency syndrome (AIDS) has been linked to the human immunodeficiency virus (HIV), which is capable of selective infection and suppression of the host immune system. The immune defect renders the human body susceptible to opportunistic infections and cancer development, which are ultimately fatal. The spread of HIV throughout the world is rapid, with no effective therapeutics on hand. It is suggested that NaPA, a nontoxic natural compound capable of glutamine depletion in vivo, could potentially be used in the treatment and prevention of AIDS.

HIV is a retrovirus. The production of retroviruses is dependent on transcriptional activation by the long terminal repeat (LTR) element, and the availability of glutamine (Gln) for translational control. Experimental data obtained with chronically infected cultured cells and animal models indicate that virus replication is inhibited specifically in cells starved for glutamine, but not for other amino acids (Gloger and Panet (1986); (J. Gen. Virol. 67:2207–2213) Roberts and McGregor, (1991), (J. Gen. Virol 72:2199–305). The results could not be attributed to either an effect on cell cycle or a general inhibition of protein synthesis.

The reason why glutamine depletion leads to virus suppression cab be explained as follows. Replication competent murine retroviruses contain an amber termination codon at the junction of gag and pol genes, which can be recognized by amber suppressor tRNA$^{Gln}$. Glutamine is thus essential for the readthrough of viral mRNA transcripts (Yoshinaka et al (1985)); PNAS 82:1618–1622 reduction in glutamine concentrations disrupts viral mRNA translational readthrough and protein synthesis, with subsequent inhibition of viral assembly and secondary spread. Although human retroviruses are somewhat different from the murine viruses studied, it has been shown that reduction in the levels of amber suppressor tRNA$^{Gln}$ in human cells infected with HIV causes a significant reduction in the synthesis of viral proteins [(Muller et al Air Research and Human Retroviruses 4:279–286 1988)]. Such data suggest that agents which can lower glutamine levels in humans, are likely to benefit patients infected with HIV. NaPA may be such as agent, since it is known to conjugate to glutamine in humans with subsequent renal excretion of phenylacetylglutamine. Since NaPA possesses also antitumor activities, the drug is likely to affect Kaposi's sarcomas, the tumors found in as many as 30% of all AIDS patients, as well as lymphoma associated with AIDS.

EXAMPLE 13

Evidence from experimental model systems in support the above hypotheses include: (a) Our preliminary findings with cultured cells indicate that NaPA can inhibit expression of genes controlled by the retroviral LTR; (b) While animal studies have been hindered by the fact that glutamine depletion by NaPA is limited to humans and high primates, an acceptable animal model (other than primates) involves rodents treated with glutaminase. Glutaminase is a bacterial enzyme that causes reduction of extracellular (and presumably intracellular) glutamine concentrations. Glutaminase treatment of viremic mice infected with Rouscher murine leukemia virus (RLV) inhibited retroviral replication and the development of splenomegaly, and significantly increased animal survival [Roberts and McGregor J. Gen. Virology 72:299–305 (1991)]. The efficacy of glutaminase therapy compared favorably with AZT, the drug currently used for treatment of AIDS. The results are of particular interest since the RLV serves as a model in the search for anti-HIV drugs (Ruprecht et al, 1986). Unfortunately, however, glutamine depletion by glutaminase in vivo is only transient due to development of neutralizing antibodies to the enzyme; once this occurs, viral replication can resume, eventually killing the host. NaPA, unlike the bacterial glutaminase, is a natural component of the human body, and thus is less likely to induce the production of neutralizing antibodies; (c) There is clinical evidence for sustained reduction by NaPA of plasma glutamine concentrations. NaPA is currently being used for treatment of hyperammonemia associated with inborn disorders of urea metabolism. The clinical experience indicate that long-term treatment with NaPA effectively reduces glutamine levels. Such treatment is nontoxic and well tolerated even by newborns. In conclusion, we propose that NaPA might benefit patients with HIV infection. NaPA could inhibit viral replication through (among other mechanisms) inhibition of LTR and depletion of glutamine, the aminoacid required for appropriate processing of viral proteins. If NaPA proves to have anti-HIV activities in humans, it could be used to prevent disease progression in asymptomatic HIV-positive individuals. The lack of toxicity, easy oral administration and relatively low cost, uniquely qualify NaPA as a chemopreventive drug. In fact, the drug is so well tolerated by humans that treatment can start just a few hours after birth. In addition, NaPA could be used (alone or in combination with other drugs) in treatment of AIDS-associated disorders including opportunistic infections, HIV encephalopathy, and neoplasia.

SECTION C
INDUCTION OF FETAL HEMOGLOBIN SYNTHESIS IN β-CHAIN HEMOGLOBINOPATHY BY PHENYLACETATE AND ITS DERIVATIVES

There is considerable interest in identifying nontoxic therapeutic agents for treatment of severe β-chain hemoglobinopathies. Employing the human leukemic K562 cell line as a model, we have explored the cellular responses to NaPA, an amino acid derivative essentially nontoxic to humans. Treatment of cultures with pharmacologically attainable concentrations of NaPA resulted in time- and dose dependent inhibition of cell proliferation and caused an increase in hemoglobin production. Molecular analysis revealed accumulation of the fetal form of hemoglobin (HbF), which was associated with elevated steady-state levels of gamma globin mRNA. All NaPA effects reversed upon cessation of treatment. Interestingly, addition of NaPA to other antitumor agents of clinical interest, i.e., 5-azacytidine and hydroxyurea, resulted in superinduction of HbF biosynthesis. The results suggest that NaPA, an agent known to be well tolerated by newborns, could be used alone or in combination with other drugs for long-term treatment of some inborn blood disorders. The pathophysiology of inherited blood disorders such as sickle cell anemia and severe β-thalassemias is based on genetic abnormalities in the β-globin gene which result in deficient or absent β-globin synthesis. The latter prevents the production of hemoglobin and results in ineffective red blood cell production and circulation. Recent data indicate that pharmacological manipulation of the kinetics of cell growth and differentiation might have beneficial effect in patients with the β-chain hemoglobinopathies, due to the induction of fetal hemoglobin (HbF) synthesis. To date, several antitumor drugs including 5-azacytidine (5AzaC), 5-aza-2'-deoxycytidine (5AzadC), hydroxyurea (HU), vinblastine, and arabinosylcytosine (ara-C) have been shown to increase the production of HbF in experimental models [Dover, Ann NY Acad Sci 612:184–190 (1990)]. Moreover, there is clinical evidence for 5AzaC and HU activity in sever β-thalassemia and sickle cell anemia, respectively. However, concerns regarding toxic and potential carcinogenic effects of the prevailing antitumor drugs raise the need to identify safe alternatives for long-term treatment of the inborn non-malignant diseases. The accumulation of fetal hemoglobin in adults is thought to be due to changes in the kinetics of erythroid differentiation rather than a direct effect on the fetal globin genes. According to this hypothesis, other agents that can induce differentiation would also be expected to affect HbF production. The focus here is on the efficacy of a novel nontoxic differentiating agent, sodium phenylacetate (NaPA).

As discussed in Section A Applicant's laboratory has found that NaPA can also affect the maturation (i.e., differentiated state) of various animal and human cell types. The drug caused growth arrest and reversal of malignant properties in a variety of in vitro tumor models including cell lines established from adenocarcinomas of the prostate and lung, malignant melanomas, and astrocytomas. Moreover, NaPA treatment was associated with adipocyte conversion in premalignant mesenchymal C3H 10T1/2 cells, and granulocyte differentiation in promyelocytic leukemia HL-60 cultures. Studies indicated that NaPA, in contrast to the chemotherapeutic differentiating drugs 5AzaC and 5AzadC, may be free of adverse effects such as cytotoxicity and tumor progression.

Indeed, NaPA is well tolerated by humans as indicated by the vast clinical experience with NaPA is in the treatment of hyperammonemia in infants with inborn errors of ureagenesis. The clinical experience indicates that acute or long-term treatment with high doses of NaPA is essentially free of adverse effects. The lack of toxicity and the ability to induce cellular differentiation prompted Applicant to examine the effect of NaPA on HbF expression.

EXAMPLE 14

The experimental system involved the human leukemic K562 cells, which carry a nonfunctional β-globin gene, but produce low levels of the fetal gamma globin and of HbF. The K562 cell line was originally established from a patient with chronic myelogenous leukemia in the blast cells transformation, and has since been extensively utilized as a model in studies of erythroid differentiation and regulation of the gamma globin gene expression. We show here for the first time that pharmacologically attainable concentrations of NaPA can promote HbF biosynthesis in the human leukemic cells, and can cause superinduction when combined with the other chemotherapeutic agents of interest, 5AzaC and HU.

MATERIALS AND METHODS

Cell Culture and reagents. The human leukemia K562 cells were maintained in RPMI 1640 medium supplemented with 10% heat-inactivated fetal calf serum (Gibco), 50 U/ml penicillin, 50 ug/ml streptomycin, and 2 mM L-glutamine unless otherwise indicated. The suspension cultures were kept in exponential growth phase by diluting every 3–5 days with fresh medium, and cell viability was determined by trypan blue exclusion. Phenylacetic acid, 4-hydroxyphenyl acetic acid, 3,4-dihydroxyphenyl acetic acid, 2,5-dihyroxyphenyl acetic acid (Sigma, St. Louis Mo.) and PAG (a gift from L. Trombetta, Houston Tex.) were dissolved in distilled water, and brought to pH 7.0 by the addition of NaOH, DON, acivicin, 5AzadC, 5AzaC, and HU (Sigma) were also dissolved in distilled. All drug stock solutions were stored in aliquots at −20° C. until used.

Determination of Hemoglobin Production. K562 cells were seeded at $1\times10^5$ cells/ml and treated with the drugs for four to seven days prior to assay. Qualitative estimation of hemoglobin production was determined by benzidine staining of intact cells in suspension. The hemoglobin concentration within cells was determined by the protein absorption at 414 nm ( ). Briefly, $1\times10^7$ cells were lysed in 1 ml of lysing buffer (0.12% Tris pH 7.4, 0.8% NaCl, 0.03% Mg-acetate, and 0.5% Np-40), vortexed and incubated on ice gor 15 minutes. The lysate were then centrifuged for 15 minutes at 1500 rpm at 4° C., and the absorption of the supernatant monitored between 350 nm and 650 nm using Beckman Du-7 scanning spectrophotometer. The hemoglobin was quantitated using the relationship of 1.0 optical density (OD) at 414 nm corresponding to 0.13 mg/ml hemoglobin as described before.

Northern Blot Analysis and DNA probes. Cytoplasmic RNA was prepared from cultures at logarithmic phase of growth and separated on 1% agarose-formaldehyde gels. Gel electrophoresis, transfer of RNA onto nytran membranes (Schleicher & Schuell), hybridization with radiolabeled DNA probes, and autoradiography (Kodak X-ray film XAR5) were according to established procedures. The probe for gamma globin was a 0.6 Kb Eco RI/Hind III fragment of the human gamma globin gene. Probes were labeled with [$^{32}$P]dCTP (NEN) using random primed DNA labeling kit (Boehringer Mannheim, West Germany).

Analysis of HbF Protein Synthesis. Newly synthesized proteins were labeled with $^{35}$S-methionine and the HbF immunoprecipitated and analyzed as previously described. Briefly, cells ($1\times10^6$ per point in 1 ml) were first subjected to 1 hr starvation in methionine-free medium, then incubated in the presence of 100 uCi/ml of $^{35}$S-methionine for 2 hrs. The labeled cells were harvested, washed and lysed in a lysing buffer containing 10 mM phosphate buffer pH 7.4, 1% Triton X100, 0.1% SDS, 0.5% deoxychilate, 100 mM NaCl, 0>1% NaN3, 2 mM PMSF, and 10 ug/ml lenpeptin. $1\times10^7$ cpm of TCA precipitable count of cytoextract was incubated with rabbit anti-human HbF (Pharmacia) and protein A Sepharose at 4° C., and the immunoprecipitates were separated by electrophoresis on 12% SDS-polyacrylamide gels.

RESULTS

The Effect of NaPA and Analogues on Cell Growth and Differentiation. Treatment of the K562 cultures with NaPA resulted in dose dependent inhibition of cell proliferation, with 1.4 mg/ml causing 50% reduction in cell number after four days of treatment. No toxicity was observed with doses as high as 2.0 mg/ml. In addition to the cytostatic effect, NaPA also induced erythroid differentiation, as indicated by an increase in the number of benzidine-positive cells (FIG. 5) and confirmed by quantitative analysis of hemoglobin production (Table 9). Similar treatment with PAG, which is the glutamine conjugated form of NaPA, had no significant effect on either cell proliferation or hemoglobin accumulation suggesting that the changes associated with NaPA treatment are specific and not due to alterations in culture conditions.

The effect of NaPA on cell growth and differentiation could be mimicked by the use of 4-hydroxyphenylacetate (Table 10). This was in marked contrast to the analogues 3,4-dihydroxyphenylacetate and 2,5-dihyroxyphenylacetate, which were highly toxic to the cells (LD50 of 60 and 100 ug/ml, respectively), and did not induce differentiation.

Regulation of Fetal Hemoglobin Production by NaPA. K562 cells normally express low but detectable levels of HbF. Protein analysis employing anti-HbF antibodies revealed significantly increased amounts of HbF in cells treated with NaPA compared to untreated controls; this was associated with elevated steady-state levels of the fetal gamma globin mRNA. The effect of NaPA on HbF production was time and dose dependent, and apparently reversible upon cessation of treatment.

Glutamine Starvation and HbF Production. NaPA treatment of humans can lead to depletion of circulating glutamine due to conjugation to glutamine and formation of PAG, an enzymatic reaction known to take place in the liver and kidney. The in vivo reduction in plasma glutamine was mimicked in vitro by culturing the K562 cells in the presence of lowered glutamine concentrations. Results presented in Table 9 show, in agreement with previous reports, that glutamine starvation alone can affect the growth rate as well as HbF production in the K562 cells. Addition of NaPA to the glutamine-depleted growth medium further augmented the cytostatic and differentiating effects observed. We speculate therefore that the effect of NaPA on erythroid differentiation and HbF production in humans may be even more dramatic than that observed with the in vitro model, due to depletion of circulating glutamine and a direct effect on the erythroid progenitor cells.

Potentiation by NaPA of Erythroid Differentiation induced by Other Chemotherapeutic Drugs. There is considerable interest in the use of 5AzaC, 5AzadC and HU for treatment of sickle cell anemia and β-thalassemia; however, the clinical use of these drugs is often limited by unacceptable toxicities. Combination treatments with nontoxic differentiating agents like NaPA could enhance hemoglobin production while minimizing the adverse effects. We tested therefore the efficacy of various combinations of NaPA with the other drugs of clinical interest. Results, summarized in Table 10, show that addition of NaPA 800 ug/ml, to low doses of 5AzadC or HU act synergitically to further augment HbF production with no toxic effect to cells. The concentration of HU used in these experiments is comparable to the plasma HU levels measured in sickle cell anemia patients following an oral administration of 25 mg/kg [(Goldberg et al. New England J Med 323:366–372 (1990)]. As to NaPA, pharmacokinetics studies in children with urea cycle disorders indicate that plasma levels of approximately 800 ug/ml can be obtained by infusion with 300–500 mg/kg/day, a treatment well tolerated even by newborns.

DISCUSSION

Chemotherapeutic agents selected for their low cytotoxic/mutagenic potential could be used for induction of fetal hemoglobin in patients with congenital sever anemias such as sickle cell and β-thalassemia. Drug toxicity is an important consideration in view of overall health condition and the variable life-span of patients with these nonmalignant blood disorders. Unfortunately, recombinant human erythropoietin, which has proved to be both nontoxic and effective therapy for anemia associated with chronic renal disease, is apparently ineffective in the treatment of sickle cell anemia. The application of other active drugs such as 5AzadC, HU, vinblastine and ara-C has been hindered by concerns regarding their carcinogenic effects. HU is also difficult to use because of the narrow margin between toxicity and the desired effect on increased HbF production [(Dover, et al., Blood 67:735–738 (1986)]. By contrast, NaPA, shown here to affect HbF production, is so well tolerated by humans that treatment can be initiated just a few hours after birth.

Using an in vitro model involving human leukemic K562 cells, we have demonstrated that NaPA can promote the maturation of early erythroid progenitor cells that have an active HbF program. Addition of NaPA to other therapeutic agents currently in clinical use, i.e., 5AzaC, 5AzadC, or HU resulted in superinduction of HbF synthesis. 5AzaC has been shown to be less toxic and more effective than HU in stimulating HbF production. Moreover, 5AzaC, unlike HU, is effective in treatment of both sickle cell anemia and β-thalassemia. Such data are consistent with the interpretation that 5AzaC acts by both perturbation of erythropoiesis and by its effect on DNA methylation. However, while hypomethylation can lead to gene activation and cell differentiation, it can also promote oncogenesis and the evolution of cells with metastatic capabilities. Our results obtained with the K562 erythroid progenitor cells indicate that the therapeutic effects of NaPA compare favorably with those of 5AzadC, yet NaPA (unlike the cytosine analog) did not cause tumor progression. Moreover, NaPA was shown to prevent tumor progression induced by 5AzadC.

The data presented here suggest that NaPA, used alone or in combination with other drugs, might be of value in treatment of leukemias and β-chain hemoglobinopathies. In addition to promoting the production of red blood cells expressing HbF through nontoxic mechanisms, NaPA may also minimize the adverse effects of other antitumor drugs currently in clinical use.

TABLE 9

HbF Accumulation in Treated K562 Cells

| Treatment (mg/ml) increase | Benzidine Positive Cells | | HbF production | |
|---|---|---|---|---|
| | (%) | fold increase | (pg/cell) | fold |
| None | 2.2 ± 0.8 | 1 | 0.35 ± 0.06 | 1 |
| NaPA | | | | |
| 0.4 | 2.7 ± 0.2 | 1.2 | 0.49 ± 0.02 | 1.4 |
| 0.8 | 7.0 ± 0.3 | 3.2 | 1.15 ± 0.20 | 3.3 |
| 1.6 | 14.6 ± 0.2 | 6.6 | 2.40 ± 0.16 | 6.8 |
| 4HP 1.6 | 14.2 ± 0.5 | 6.45 | ND | |
| PAG 2.6 | 2.1 ± 0.5 | 0.95 | 0.37 ± 0.03 | 1.06 |

TABLE 10

Glutamine Starvation and HbF Production

| | HbF (pg/cell) | |
|---|---|---|
| Gln (mM) | Gln starvation alone | plus NaPA (0.8 mg/ml) |
| 2.0 | 0.39 ± 0.04 | 1.0 ± 0.06 |
| 0.5 | 0.56 ± 0.01 | 1.15 ± 0.01 |
| 0.2[a] | 1.17 ± 0.12 | 1.75 ± 0.22 |
| 0.1[a] | 1.86 ± 0.40 | 2.22 ± 0.20 |

[a]The concentration of NaPA used in this study (0.8 mg/ml) is pharmacologically attainable without toxicity. In children such a treatment is expected to cause a drop in circulating glutamine plasma levels to 0.1–0.2 mM. The results presented above indicate that under such conditions HbF production increases 4.5–5.7 fold compared to controls. We propose therefore that the effect of NaPA in children might be more dramatic then that seen under routine culture conditions (i.e., cell growth in medium with 2 mM Gln).

TABLE 11

Potentiation by NaPA of HU's Therapeutic Effect

| Treatment | HbF (pg/cell) |
|---|---|
| none | 0.39 ± 0.04 |
| NaPA (0.8 mg/ml) | 1.64 ± 0.07 |
| HU (50 uM) | 1.00 ± 0.03 |
| HU (50 uM) + NaPA | 5.91 ± 0.6[b] |
| HU (100 uM) | 2.12 ± 0.04 |
| HU (100 uM) + NaPA | 6.71 ± 0.05[b] |

[a]To mimic the effect of NaPA in vivo, treatments involving NaPA were performed in medium supplemented with 0.2 mM Gln (see explanation to table 2). Control untreated cells and those treated with HU or 5AzadC alone were maintained in growth medium with 2 mM gln.
[b]The results indicate that NaPA and HU act synergistically to induce HbF Production in the erytroid progenitor cells
Note: Similar results have been obtained for the combination NaPA 0.8 mg/ml and 5AzadC 0.3 uM.

Contemplated Models of Drug Administration

NaPA may be administered locally or systemically. Systemic administration means any or route of administration which results in effective levels of active ingredient appearing in the blood or at a site remote from the site of administration of said active ingredient.

The pharmaceutical formulation for systemic administration according to the invention may be formulated for intravenous, intramuscular, sub-cutaneous, oral, nasal, enteral, parenteral or topical administration. In some cases, combination of types of formulations may be used simultaneously to achieve systemic administration of the active ingredient.

Suitable formulations for oral administration include hard or soft gelatin capsules, dragees, pills, tablets, including coated tablets, elixirs, suspensions, and syrups or inhalations.

Solid dosage forms in addition to those formulated for oral administration include rectal suppositories.

The compounds of the present invention may also be administered in the form of an implant.

Suitable formulations for topical administration include creams, gels, jellies, mucilages, pastes and ointments.

Suitable injectable solutions include intravenous, subcutaneous, and intramuscular injectable solutions. The compounds of the present invention may also be administered in the form of an infusion solution or as a nasal inhalation or spray.

The compounds of the present invention may also be used concomitantly or in combination with selected biological response modifiers, e.g., interferons, interleukins, tumor necrosis factor, glutamine antagonists, hormones, vitamins, as well as anti-tumor agents and hematopoetic growth factors, discussed above.

It has been observed that NaPA is somewhat malodorous. Therefore, it may be preferable to administer this compound in the presence of any of the pharmaceutically acceptable odor-masking excipients or as its precursor phenylbutyrate which has no offensive odor.

The PAA and its pharmaceutically acceptable derivatives to be used as antitumor agents can be prepared easily using pharmaceutical materials which themselves are available in the art and can be prepared by established procedures. The following preparations are illustrative of the preparation of the dosage forms of the present invention, and are not to be construed as a limitation thereof.

EXAMPLE 14
PARENTERAL SOLUTION

A sterile aqueous solution for parenteral administration containing 200 mg/ml of NaPA for treating a neoplastic disease is prepared by dissolving 200 g. of sterilized, micronized NaPA in sterilized Normal Saline Solution, qs to 1000 ml. The resulting sterile solution is placed into sterile vials and sealed. The above solution can be used to treat malignant conditions at a dosage range of from about 100 mg/kg/day to about 1000 mg/kg/day. Infusion can be continuous over a 24 hour period.

EXAMPLE 15
PARENTERAL SOLUTION

A sterile aqueous solution for parenteral administration containing 50 mg/ml of NaPA is prepared as follows:

| Ingredients | Amount |
|---|---|
| NaPA, micronized | 50 g. |
| Benzyl alcohol | 0.90% w/v |
| Sodium chloride | 0.260% w/v |
| Water for injection, qs | 1000 ml |

The above ingredients, except NaPA, are dissolved in water and sterilized. Sterilized NaPA is then added to the sterile solution and the resulting solution is placed into sterile vials and sealed. The above solution can be used to treat a malignant condition by administering the above solution intravenously at a flow rate to fall within the dosage range set forth in Example 14.

EXAMPLE 16
PARENTERAL SOLUTION

A sterile aqueous solution for parenteral administration containing 500 mg/ml of sodium phenylbutyrate is prepared as follows:

| Ingredients | Amount |
|---|---|
| Sodium phenylbutyrate | 500 g. |
| Dextrose | 0.45% w/v |
| Phenylmercuric nitrate | 0.002% w/v |
| Water for injection, qs | 1000 ml. |

The preparation of the above solution is similar to that described in Examples 14 and 15.

EXAMPLE 17

TABLET FORMULATION

A tablet for oral administration containing 300 mg of NaPA is prepared as follows:

| Ingredients | Amount |
| --- | --- |
| NaPA | 3000 g. |
| Polyvinylpyrrolidone | 225 g. |
| Lactose | 617.5 g. |
| Stearic acid | 90 g. |
| Talc | 135 g. |
| Corn starch | 432.5 g. |
| Alcohol | 45 L |

NaPA, polyvinylpyrrolidone and lactose are blended together and passed through a 40-mesh screen. The alcohol is added slowly and the granulation is kneaded well. The wet mass is screened through a 4-mesh screen, dried overnight at 50° C. and screened through a 20-mesh screen. The stearic acid, talc and corn starch is bolted through 60-mesh screen prior to mixing by tumbling with the granulation. The resulting granulation is compressed into tablets using a standard 7/16 inch concave punch.

EXAMPLE 18

TABLET FORMULATION

A tablet for oral administration containing 200 mg of sodium phenylbutyrate is prepared as follows:

| Ingredients | Amount |
| --- | --- |
| Sodium phenylbutyrate | 2240 g. |
| Compressible sugar (Di-Pac) | 934 g. |
| Sterotex | 78 g. |
| Silica gel (Syloid) | 28 g. |

The above ingredients are blended in a twin-shell blender for 15 minutes and compressed on a 13/22 inch concave punch.

EXAMPLE 19

INTRANASAL SUSPENSION

A 500 ml sterile aqueous suspension is prepared for intranasal installation as follows:

| Ingredients | Amount |
| --- | --- |
| NaPA, micronized | 30.0 g. |
| Polysorbate 80 | 2.5 g. |
| Methylparaben | 1.25 g. |
| Propylparaben | 0.09 g. |
| Deionized water, qs | 500 ml |

The above ingredients, with the exception of NaPA, are dissolved in water and sterilized by filtration. Sterilized NaPA is added to the sterile solution and the final suspensions are aseptically filled into sterile containers.

EXAMPLE 20

OINTMENT

An ointment is prepared from the following ingredients:

| Ingredients | Amount |
| --- | --- |
| NaPA | 10 g. |
| Stearyl alcohol | 4 g. |
| White wax | 8 g. |
| White petrolatum | 78 g. |

The stearyl alcohol, white wax and white petrolatum are melted over a steam bath and allowed to cool. The NaPA is added slowly to the ointment base with stirring.

EXAMPLE 21

LOTION

| Ingredient | Amount |
| --- | --- |
| Sodium phenylbutyrate | 1.00 g. |
| Stearyl methylcellulose (4,500) solution (2%) | 25.00 ml. |
| Benzalkonium chloride | 0.03 g. |
| Sterile water | 250.00 ml |

The benzalkonium chloride is dissolved in about 10 ml. of sterile water. The sodium phenylbutyrate is dispersed into methylcellulose solution by means of vigorous stirring. The methylcellulose (4,500) used is a high viscosity grade. The solution of benzalkonium chloride is then added slowly while stirring is continued. The lotion is then brought up to the desired volume with the remaining water. Preparation of the lotion is carried out under aseptic conditions.

EXAMPLE 22

DUSTING POWDER

| Ingredients | Amount |
| --- | --- |
| NaPA | 25 g. |
| Sterilized absorbable maize starch BP dusting powder | 25 g. |

The dusting powder is formulated by gradually adding the sterilized absorbable dusting powder to NaPA to form a uniform blend. The powder is then sterilized in conventional manner.

EXAMPLE 23

SUPPOSITORY, RECTAL AND VAGINAL PHARMACEUTICAL PREPARATIONS

Suppositories, each weighing 2.5 g. and containing 100 mg. of NaPA are prepared as follows:

| Ingredients | Amount/1000 |
| --- | --- |
| suppositories | |
| NaPA, micronized | 100 g. |
| Propylene glycol | 150 g. |
| Polyethylene glycol 4000, qs | 2500 g. |

NaPA is finely divided by means of an air micronizer and added to the propylene glycol and the mixture is passed through a colloid mill until uniformly dispersed. The polyethylene glycol is melted and the propylene glycol dispersion added slowly with stirring. The suspension is poured into unchilled molds at 40° C. Composition is allowed to cool and solidify and then removed from the mold and each suppository is foil wrapped.

The foregoing suppositories are inserted rectally or vaginally for treating neoplastic disease.

It is known that intracellular glutathione plays a major role in detoxification and repair of cellular injury by chemical and physical carcinogens. NaPA treatment of normal or tumor cells markedly induced the activity of intracellular glutathione approximately 2–10 fold depending on growth conditions. Nontoxic agents that can induce glutathione are highly desirable since these are likely to protect cells from damage by a variety of chemical carcinogens and ionizing radiation.

Taken together, the present invention demonstrates that NaPA has valuable potential in cancer prevention in cases such as high risk individuals, for example, heavy smokers with familial history of lung cancer, inherited disorders of oncogene abnormalities (Li-Fraumeni syndrome), individuals exposed to radiation, and patients in remission with residual disease. Furthermore, NaPA can be used in combination with other therapeutic agents, such as chemicals and radiation, to enhance tumor responses and minimize adverse effects such as cytotoxicity and carcinogenesis. The antitumor activity, lack of toxicity, and easy administration qualify NaPA as a preferred chemopreventive drug.

What is claimed:

1. A method of inhibiting the growth of a rapidly proliferating nonmalignant or malignant mammalian tumor cell sensitive to a compound recited below in a host in need of such inhibition, comprising administering to the host an amount effective to attain said inhibition of said compound having the formula (I):

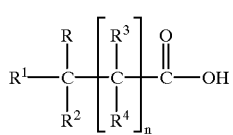

wherein

R and $R^1$ are independently H, lower alkoxy, or lower alkyl;

$R^2$ is phenyl, unsubstituted or substituted with halogen, hydroxy, or lower alkyl;

$R^3$ and $R^4$ are H; and n is 0 or 2;

or a pharmaceutically acceptable salt thereof.

2. The method of claim 1, wherein the pharmaceutically acceptable salt is an alkali metal salt or alkaline earth metal salt.

3. The method of claim 1, wherein R is H and $R^1$ is H, $CH_3O$, $CH_3$, $C_2H_5$, or $C_3H_7$.

4. The method of claim 1, wherein R is H and $R^1$ is H.

5. The method of claim 1, wherein $R^2$ is phenyl or phenyl substituted with from 1 to 4 halogens, from 1 to 4 hydroxy moieties, or from 1 to 2 methyl moieties.

6. The method of claim 1, wherein $R^2$ is phenyl or phenyl substituted with from 1 to 4 halogens of Cl or F, from 1 to 4 hydroxy moieties, or from 1 to 2 methyl moieties.

7. The method of claim 1, wherein $R^2$ is phenyl, 3-methylphenyl, 4-methylphenyl, 2,6-dimethylphenyl, 3-chlorophenyl, 4-chlorophenyl, 2,6-dichlorophenyl or 4-fluorophenyl.

8. The method of claim 1, wherein $R^2$ is phenyl.

9. The method of claim 1, wherein the compound is the sodium salt of phenylacetate, phenylbutyrate, 3-chlorophenylacetate, 4-chlorophenylacetate, 2,6-dichlorophenylacetate, or 4-fluorophenylacetate.

10. The method of claim 1, wherein the compound is the sodium salt of formula I and R is H, $R^1$ is H, and $R^2$ is phenyl.

11. The method of claim 1, wherein the compound is sodium phenylacetate.

12. The method of claim 1, wherein the compound is sodium phenylbutyrate.

13. The method of claim 1, wherein n is 0.

14. The method of claim 1, comprising administering a pharmacologically-effective amount of the compound to the host to suppress the growth of the nonmalignant or malignant tumor cell.

15. The method of claim 1, wherein the compound is administered intravenously at a dosage level of from about 50 mg/kg/day to about 1,000 mg/kg/day.

16. The method of claim 1, wherein the compound is administered subcutaneously at a dosage level of from about 50 mg/kg/day to about 1,000 mg/kg/day.

17. The method of claim 1, wherein the compound is administered orally at a dosage level of from about 50 mg/kg/day to about 1,000 mg/kg/day.

18. The method of claim 1, wherein the compound is applied topically at a dosage concentration of from about 1 to about 10 mg/ml.

19. The method of claim 1, wherein the tumor is a prostatic carcinoma tumor, melanoma tumor, glial brain tumor, Kaposi's sarcoma tumor or lymphoma tumor, leukemic tumor, lung adenocarcinoma tumor, breast cancer tumor, osteosarcoma tumor, fibrosarcoma tumor, or squamous cancer tumor.

20. The method of claim 1, wherein the host is a human.

21. A method of inhibiting the growth of a rapidly proliferating nonmalignant or malignant mammalian tumor cell sensitive to a compound recited below in a host in need of such inhibition, comprising administering to the host an amount effective to attain said inhibition of said compound of phenylacetic acid or phenylbutyric acid or a pharmaceutically acceptable salt thereof.

22. The method of claim 21, wherein the tumor is a prostatic carcinoma tumor, melanoma tumor, glial brain tumor, Kaposi's sarcoma tumor or lymphoma tumor, leukemic tumor, lung adenocarcinoma tumor, breast cancer tumor, osteosarcoma tumor, fibrosarcoma tumor, or squamous cancer tumor.

23. A method of inhibiting the growth of a rapidly proliferating nonmalignant or malignant mammalian tumor sensitive to a compound recited below in a host in need of said inhibition, consisting essentially of administering to the host an amount effective to attain said inhibition of said compound having the formula (I):

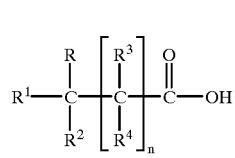

wherein

R and $R^1$ are independently H, lower alkoxy, or lower alkyl;

$R^2$ is phenyl, unsubstituted or substituted with halogen, hydroxy, or lower alkyl;

$R^3$ and $R^4$ are H; and n is 0 or 2;

or a pharmaceutically-acceptable salt thereof.

24. The method of claim 23, wherein the compound is phenylacetic acid or phenylbutyric acid or a pharmaceutically acceptable salt thereof.

25. The method of claim 23, wherein n is 0.

26. The method of claim 23, wherein the tumor is a prostatic carcinoma tumor, melanoma tumor, glial brain tumor, Kaposi's sarcoma tumor or lymphoma tumor, leukemic tumor, lung adenocarcinoma tumor, breast cancer tumor, osteosarcoma tumor, fibrosarcoma tumor, or squamous cancer tumor.

27. A method of treating a host afflicted with a condition of cancer sensitive to a compound recited below, comprising administering to said host a pharmacological amount effective to ameliorate said condition of said compound having the formula (I):

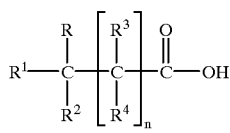

(I)

wherein

R and $R^1$ are independently H, lower alkoxy, or lower alkyl;

$R^2$ is phenyl, unsubstituted or substituted with halogen, hydroxy, or lower alkyl;

$R^3$ and $R^4$ are H; and n is 0 or 2;

or a pharmaceutically-acceptable salt thereof.

28. The method of claim 27, wherein the compound is phenylacetic acid or phenylbutyric acid or a pharmaceutically acceptable salt thereof.

29. The method of claim 27, wherein n is 0.

30. The method of claim 27, wherein the cancer is a prostatic cancer, melanoma, glial brain tumor, Kaposi's sarcoma or lymphoma, leukemia, lung adenocarcinoma, breast cancer, osteosarcoma, fibrosarcoma, or squamous cancer.

31. A method of inducing differentiation of a tumor cell sensitive to a compound recited below in a host in need of such treatment comprising administering to said host a therapeutically effective amount of said compound having the formula (I):

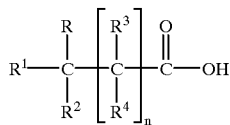

(I)

wherein

R and $R^1$ are independently H, lower alkoxy, or lower alkyl;

$R^2$ is phenyl, unsubstituted or substituted with halogen, hydroxy, or lower alkyl;

$R^3$ and $R^4$ are H; and n is 0 or 2;

or a pharmaceutically-acceptable salt thereof.

32. The method of claim 31, wherein the compound is phenylacetic acid or phenylbutyric acid or a pharmaceutically acceptable salt thereof.

33. The method of claim 31, wherein n is 0.

34. The method of claim 31, wherein the tumor is a prostatic carcinoma tumor, melanoma tumor, glial brain tumor, Kaposi's sarcoma tumor or lymphoma tumor, leukemic tumor, lung adenocarcinoma tumor, breast cancer tumor, osteosarcoma tumor, fibrosarcoma tumor, or squamous cancer tumor.

35. A method of treating a malignant condition sensitive to a compound recited below in a host in need of such treatment comprising administering to the host a therapeutically effective amount of said compound having the formula (I):

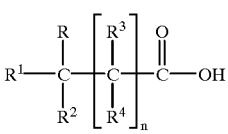

(I)

wherein

R and $R^1$ are independently H, lower alkoxy, or lower alkyl;

$R^2$ is phenyl, unsubstituted or substituted with halogen, hydroxy, or lower alkyl;

$R^3$ and $R^4$ are H; and n is 0 or 2;

or a pharmaceutically-acceptable salt thereof.

36. The method of claim 35, wherein the compound is phenylacetic acid or phenylbutyric acid or a pharmaceutically acceptable salt thereof.

37. The method of claim 35, wherein n is 0.

38. The method of claim 35, wherein the malignant condition to be treated is a prostatic cancer, melanoma, glial brain tumor, Kaposi's sarcoma or lymphoma, leukemia, lung adenocarcinoma, breast cancer, osteosarcoma, fibrosarcoma, or squamous cancer.

39. The method of claim 35, wherein the malignant condition to be treated is prostatic cancer.

40. The method of claim 35, wherein the malignant condition to be treated is melanoma.

41. The method of claim 35, wherein the malignant condition to be treated is a glial brain tumor or Kaposi's sarcoma or lymphoma.

* * * * *